US005616467A

United States Patent [19]

Olsen et al.

[11] Patent Number: 5,616,467
[45] Date of Patent: *Apr. 1, 1997

[54] METHOD AND KIT FOR ANALYTE DETECTION EMPLOYING GOLD-SOL BOUND ANTIBODIES

[75] Inventors: Egil Olsen, Strommen; Ørjan Olsvik, Oslo, both of Norway

[73] Assignee: Nycomed AS, Norway

[*] Notice: The term of this patent shall not extend beyond the expiration date of Pat. No. 5,556,756.

[21] Appl. No.: 458,115

[22] Filed: Jun. 2, 1995

Related U.S. Application Data

[62] Division of Ser. No. 895,244, Jun. 5, 1992, which is a continuation of Ser. No. 536,609, filed as PCT/EP89/00050, Jan. 11, 1989 abandoned.

[30] Foreign Application Priority Data

Jan. 13, 1988 [GB] United Kingdom ............... 8800702

[51] Int. Cl.$^6$ ............... G01N 33/53; G01N 33/567; G01N 33/543; G01N 33/552
[52] U.S. Cl. ............... 435/7.2; 436/518; 436/527
[58] Field of Search ............... 435/6, 7, 7.2; 436/527, 436/518

[56] References Cited

U.S. PATENT DOCUMENTS

| | | | |
|---|---|---|---|
| Re. 33,581 | 4/1991 | Nicoli et al. ............... | 435/7.2 |
| 4,299,916 | 11/1981 | Litman et al. . | |
| 4,459,361 | 7/1984 | Gefter . | |
| 4,742,000 | 5/1988 | Greene ............... | 435/7 |
| 4,744,760 | 5/1988 | Molday ............... | 424/3 |
| 4,760,017 | 7/1988 | McCormick ............... | 435/6 |
| 4,853,335 | 8/1989 | Olsen et al. ............... | 436/527 |
| 4,874,691 | 10/1989 | Chandler ............... | 435/7 |
| 4,879,220 | 11/1989 | Mrsny et al. ............... | 435/7 |
| 4,882,269 | 11/1989 | Schneider et al. ............... | 435/6 |
| 5,079,172 | 1/1992 | Hari et al. . | |

FOREIGN PATENT DOCUMENTS

| | | |
|---|---|---|
| 0158746 | 10/1985 | European Pat. Off. . |
| 0258963 | 6/1987 | European Pat. Off. ..... G01N 33/543 |
| 0250137 | 6/1987 | European Pat. Off. ..... G01N 33/558 |
| WO-A-8304314 | 12/1983 | WIPO . |

OTHER PUBLICATIONS

Wu 1981 Proc. Natl. Acad. Sci. USA 78:7059–63.
Hutchison et al. 1982 J Cell Biol 95:609–18.
Cremers 1987 Histochemistry 86:609–15.
Wolber 1988 Lab Invest 59:144–51.
Tomlinson et al. 1988 Anal Biochem 171:217–22.
Bhatt et al. 1988 Nucl. Acids Res 16:3951–61.
Wolber et al. 1989 J Histochem Cytochem 37:97–104.
Brangeon et al. 1989 Planta 177:151–9.
Hamkalo 1989 Am J Anat 185:197–204.
Childs 1989 Am J Anat 185:223–35.
Cubie and Norval 1989 J Clin Pathol 42:988–91.
Geuze et al. 1981 J Cell Biol 89:653–65.
Jan W. Slot et al., "A New Method of Preparing Gold Probes for Multiple–Labelling Cytochemistry"; European Journal of Cell Biology 38, 87–93 (1985).
Jansen Life Sciences Data Sheet (1985).
Baschong et al., Chemical Abstracts 104(3): 17205j Histochemistry 83(5), 409–11 (1985).
Roth, Biosis Abst. No. 76049405, Histochem. J. 14(5) 791–802 (1982).
Surek et al. (1984) Biochemical and Biophysical Res. Comm., vol. 121, No. 1 pp. 284–289.

Primary Examiner—W. Gary Jones
Assistant Examiner—Amy Atzel
Attorney, Agent, or Firm—Bacon & Thomas

[57] ABSTRACT

A method for the qualitative or quantitative determination of an analyte in a test sample wherein a labelled reagent is caused to be immobilized in bound form on a solid phase to provide an indication of the presence or quantity of the analyte in the sample is disclosed and is characterized in that the labelled reagent comprises a gold sol bound to a substance capable of specifically binding to said analyte or to a specific binding partner therefor, at least 75% by weight of the gold particles of the gold sol having a mean diameter of less than 5 nanometers.

11 Claims, No Drawings

METHOD AND KIT FOR ANALYTE DETECTION EMPLOYING GOLD-SOL BOUND ANTIBODIES

This application is a Division of application Ser. No. 07/895,244, filed Jun. 5, 1992; which is a Continuation of application Ser. No. 07/536,609, filed as PCT/EP89/00050 Jan. 11, 1989, now abandoned.

This invention relates to a method for the qualitative or quantitative determination of the presence of an analyte in an aqueous medium.

The detection and/or assay of analytes using immunoassay techniques is well established, particularly in relation to proteins such as antigens and antibodies, as well as sugars, lectins and nucleic acids. However, many current techniques, while being of great sensitivity, are often laborious in requiring a number of steps each of which may be of long duration. It has proved possible to simplify some of such assays, however, by immobilising one of the components of the assay system on a solid support, since this facilitates removal of excess reagents. Such assays will normally involve the use of a labelled macromolecule, which may be the analyte itself or a binding partner for the analyte, carrying a suitable label such as a radioisotope, a fluorophore or an enzyme producing a characteristic reaction.

One simplification which has been proposed is to use a coloured substance attached to one of the immunoassay reactants as a visible marker. However, very few coloured substances are able to produce a sufficiently intensive signal. U.S. Pat. No. 4,313,734 of Akzona Inc. describes the use of, inter alia, colloidal gold as such a coloured material, specifying that the gold particles should have a particle size of at least 5 nanometers, preferably 10 to 100 nm.

The inventors of the Akzona-patent have subsequently published several articles which emphasise that larger particles are preferred. Thus, Leuvering et al, (J. Immunoassay, 1, 77–91, 1980) describe use of colloidal gold of 60 nm; this publication is closely related to the disclosure of the patent and states that only by higher antigen concentrations could the colour produced be seen by the naked eye. This is in accordance with a method in which the gold is extracted into solution.

The same inventors (Leuvering et al, J. Immunol. Meth. 45, 183–194, 1981; and 62, 175–184, 1983) have described how antibodies and antigens may agglutinate metal sols in solution, thereby producing changes in absorption maxima and extinction coefficients. Gold colloids in the range 40–80 nm were tested and 50 nm found to be optimal.

These inventors have also described (J. Immunol. Meth. 62, 175–184, 1983), a sandwich assay with gold colloids. Gold colloids in the range 25–70 nm were tried and 55 nm found to be optimal. This assay is based on the ordinary plate type immunoassay and is similar to the examples mentioned in U.S. Pat. No. 4,313,734.

Gribnau et al in a review (J. Chromatography, 376, 175–189, 1986) have discussed all the techniques using small particles in immunoassays. The section describing colloidal gold describes several methods but only mentions gold with diameter 50 nm.

European Patent Application 0158746A of Janssen Pharmaceutica N.V. relates to blotting overlay techniques which may be used for the assay of substances in complex mixtures. This patent describes inter alia the use of colloidal gold complexed to components which react with corresponding binding components on a solid support. However, this patent stresses the special nature of blotting overlay assays as compared with assays of analytes in aqueous solution. While it refers to use of gold or silver particles in the size range 3–100 nm, particle sizes of 5–50 nm are stated to be preferred and the examples disclose only 20 nm particles. There is no teaching of the advantage of using gold particles below 5 nm in diameter or of the actual use of such particles.

Surek and Latzko (Biochem. Biophys. Res. Comm. 121, 284–289, 1984) describe the use of colloidal gold at 5 nm and 15 nm in a certain blotting technique from electrophoretic gels. While the authors found that 5 nm gold particles produced a more sharply stained electrophoretic band of proteins than did 15 nm gold particles, they did not report the more intensive total staining, nor the more rapid reaction which we have observed.

So far, there are no publications showing that gold colloids smaller than 5 nm may be directly coupled to proteins so as to give a complex which is stable even when the protein part of it takes part in immunoassay reactions. Our experiments have shown that this is surprisingly possible. It has further been suggested that larger gold particles coated with the immunoassay reactant would have the virtue of binding relatively large amounts of the label to the analyte or other reactant. Our experiments have shown, however, that when gold particles less than 5 nm in mean diameter are used in a solid phase assay system, the rate of reaction in the immunoassay is increased in certain cases and the intensity of the colour of the immobilised gold sol is surprisingly greater than when larger gold particles are used.

According to the present invention we provide a method for the qualitative or quantitative determination of an analyte in a test sample wherein a labelled reagent is caused to be immobilised in bound form on a solid phase to provide an indication of the presence or quantity of the analyte in the sample, characterised in that the labelled reagent comprises a gold sol bound to a substance capable of specifically binding to said analyte or to a specific binding partner therefor, at least 75% by weight of the gold particles of the gold sol having a mean diameter of less than 5 nanometers.

In many types of solid phase assay it is advantageous to couple an analyte analogue or a specific binding partner for said analyte to a solid support to provide the solid phase onto which the labelled reagent is immobilised. As a further aspect of the invention therefore, we provide a method for the qualitative or quantitative determination of an analyte in a liquid sample, wherein said sample is contacted in an aqueous assay medium with (i) an analyte analogue or a specific binding partner for said analyte immobilised on a solid support and (ii) a labelled reagent comprising a gold sol attached to a molecule capable of specifically binding either said analyte or a specific binding partner for said analyte, whereby a quantity of said gold sol reagent is immobilised on said support, inspection or determination of which is used to indicate the presence or quantity of the said analyte in the sample, at least 75% by weight of the gold particles of the gold sol having a mean diameter of less than 5 nanometers.

The solid phase onto which the labelled reagent is immobilised may alternatively be inert and immobilise the bound form of the labelled reagent by trapping the latter physically, e.g. by not allowing the bound form of the labelled reagent to pass through pores in the solid phase, while allowing the unbound labelled reagent to pass through such pores.

The term "analyte analogue" as used herein will be understood to refer to any species capable of specifically binding to a specific binding partner for the analyte under assay and thus includes within its scope a further quantity of that analyte.

As indicated above, the method of the invention has the advantage of more rapid reaction of the gold sol reagent with the immobilised reactant, reflected in a shorter incubation time. Furthermore, the intensity of colour of the gold sol is surprisingly increased in systems where the reagent is filtered through the insoluble membrane support. This may be another advantage which is connected to a more rapid reaction.

The mean diameter of a particle, which may not be completely spherical, is the mean of the largest and smallest diameters of that particle. It is particularly preferred that at least 80% by weight of the gold particles have a mean diameter less than 5 nm. Certain batches of the product Colloidal Gold Sol G5 of Janssen Life Sciences Products, sold for use as a histological stain, have proved to be useful. In one specific batch, 85% of the particles were less than 5 nm in diameter, the average diameter being 4.5 nm with a Gaussian distribution between 1.1 and 7.6 nm. Gold sols with average diameters in the range 2–4 nm may also conveniently be made by slight modifications of known methodology, e.g. variation of tannic acid concentration in the procedure of Slot and Geuze (Eur. J. Cell. Biol. 38, 87–93, 1985). We have found that particles having a mean diameter of 4–4.5 nm are preferable, since smaller particles (that is particles smaller than about 3 nm) do not sediment so well during washing steps.

Our results indicate that there is an approximate 1:1 stochiometry between gold sol particles having a mean diameter less than 5 nm and antibodies to which they may be bound. This stochiometric ratio increases to more than one gold particle per antibody when the mean diameter of the particles is less than about 3 nm. This approximate 1:1 relationship may account in part for the more favourable reaction kinetics of the smaller particles when compared with prior art particles having large numbers of antibodies per gold particle. Although high ratios of antibody to gold particles can be acheived with particles of a size suggested by Leuvering et al (vide supra), the binding of one antibody to an antigen may unduly affect the availability of the other antibodies on that particle to bind other antigen molecules.

The present method can be applied to any solid phase system for detection or assay of analytes. The following types of assay are typical:

1. A sandwich assay in which component A is bound to a solid support. Test solution with analyte B is added whereby B binds to A. Gold-labelled component C is added and since C binds to B the colloidal gold is immobilised and colours the solid support.

Components A, B and C are all of receptor-ligand types in which both A and C interact with B, whereas A and C do not directly bind to each other.

2. A sandwich assay as in 1 except that the test solution with analyte B and gold-labelled component C are mixed and the mixture is added to the solid support to which component A is bound.

3. A competitive assay in which component A is bound to a solid support. Test solution with analyte B is mixed with a known amount of gold-labelled analyte B and added to the solid support. B and gold-labelled B will compete in binding to A and a reduction of the colour of colloidal gold on the solid support indicates increasing amounts of analyte B in the test solution.

4. A competitive assay as in 3, but sequential addition of test solution and gold-labelled B.

5. Excess component A is labelled with colloidal gold and mixed with test-solution containing unknown amount of analyte B. A and B then couple. The mixture is added to a porous support onto which component B is immobilized. Remaining, unbound labelled A will couple to the immobilized B on solid support.

6. Analyte B is reacted with gold labelled component C, optionally together with one or more other binding partners for analyte B to form a complex aggregate. The reaction mixture is caused to diffuse through an inert filter medium, the pores of which are too small to allow the complex aggregate to pass through but large enough to permit excess gold labelled component C to pass through.

The solid phase or support on to which the labelled reagent is caused to be immobilised can take a number of forms, of which the following are illustrative:

A plastic stick, optionally covered with pads of any porous material. The stick may be dipped in the reaction solutions in order to conduct the various steps of an assay.

The wall of a test tube, a well in a microtitre-plate or the wall of any other suitable reaction chamber.

A porous material, conveniently a membrane, in which the reaction solutions may diffuse transversely through or laterally. In the case using the filtration principle, such materials advantageously permit excess reagents to pass through and may conveniently be combined with an absorbent for such excess liquids.

Beads (including microspheres) which may be isolated by centrifugation, filtration or, where the beads contain ferromagnetic compounds, magnetism.

The coupling of the analyte analogue or specific binding partner for the analyte under assay to the support may be by covalent, electrostatic or hydrophilic means or a combination of these methods. Such methods are well established in the art.

The method of the invention may be used to detect or assay a wide range of analytes which may be selected, for example, from the following ligand-receptor pairs: antigen/antibody, hapten/antibody, hormone/hormone receptor, sugar/lectin, biotin/avidin-(streptavidin), protein A/immunoglobulin, enzyme/enzyme cofactor, enzyme/enzyme inhibitor and nucleic acid pairs (DNA-DNA, DNA-RNA or RNA-DNA). At least one of such reaction partners may be bound or complexed with other molecules. Thus, biotin or avidin or a wide range of antibodies may be coupled to other molecules to provide a means of assaying the latter. For example, a specific nucleic acid probe can be labelled via the introduction of biotinylated nucleoside triphosphates. Such a probe, after binding to analyte DNA or RNA, can then be detected or assayed by the use of avidin or streptavidin labelled with gold sol.

In general, where the analyte is one of those listed above, a binding partner for use in the method of the invention will be the other component of the pair. In sandwich systems wherein the analyte binds both to an immobilised binding partner and a binding partner labelled with gold sol, the binding partners may be the same or different. Preferably the binding partners will each be an antibody reagent directed against different, well spaced determinants of the analyte.

It will be understood that the term "antibody" as used herein includes within its scope (a) any of the various classes or sub-classes of immunoglobin, e.g. IgG, IgM, derived from any of the animals conventionally used;

(b) monoclonal antibodies; and (c) fragments of antibodies, monoclonal or polyclonal, which retain an antigen-binding site, i.e. fragments devoid of the Fc portion (e.g. Fab, Fab', F(ab'))$_2$) or the so-called "half-molecule" fragments obtained by reductive cleavage of the disulphide bonds connecting the heavy chain components in the intact antibody.

Below is a non-exhaustive list of the types of immunogens which can be detected or quantified by the method of the present invention.

| | |
|---|---|
| proteins | glycoproteins |
| nucleoproteins | peptide hormones |
| serum proteins | complement proteins |
| coagulation factors | microbiocidal products |
| viral products | bacterial products |
| fungal products | specific Immunogens |
| albumin | angiotensin |
| bradykinin | calcitonin |
| carcinoembryonic antigen | chloriomamotropin |
| chorogonadotropin | cortiocotropin |
| erythropoietin | Factor VIII |
| fibrinogin | alpha-2-H-globulin |
| follitropin | Gastrin |
| gastrin sulfate | glucagon |
| gonadotropin | haptoglobin |
| Hepatitis B surface antigen | immunoglobulins (A,D,E,G,M) |
| insulin | lipotropin |
| kallidin | |
| melanotropin | oxytocin |
| pancreozymin | placental lactogen |
| prathryin | proangiotensin |
| prolactin | somatotropin |
| relaxin | secretin |
| somatomadin | somatostatin |
| thryrotropin | vasotocin |
| thymopoietin | vasopressin |
| alpha-1-fetoprotein | alpha-2-H globulin |

Particularly interesting analytes for assay by the method of the invention are blood proteins such as fibrin degradation products e.g. $D_2$, which are bound by immunoglobulins such as IgG, and human c-reactive protein.

The analyte solution may be used directly or may be diluted, e.g. with a suitable buffer solution. The gold sol preparation may also be prepared at varying dilutions using an appropriate buffer solution, the dilutions being selected to give a colour of desired intensity (i.e. optical density or reflection) on completion of the assay procedure. It may be desirable to wash the support to remove excess reagents, e.g. with a buffer solution prior to assay, in order to reduce background colour.

Where the assay is based on the total amount of gold sol retained on the immobilised support, the colour may be estimated by a reflectometer, densitometer or similar device.

The support used to immobilise one of the binding partners in the assay or an analyte analogue may, for example, be nitrocellulose, paper or cellulose acetate activated with reagents such as cyanogen bromide and nylon modified by introduction of tertiary amino groups. Such supports are conveniently used in the form of porous membranes.

In a particularly preferred method according to the invention, the inert support is a membrane, for example a nylon membrane such as Hybond N (sold by Amersham International) which readily adsorbs proteins and which has pores which permit passage of liquid. An absorbent pad such as cellulose blotting paper is advantageously placed on one side of the membrane and a liquid impermeable sheet, preferably white, placed over the pad. A similar liquid impermeable sheet is placed over the other side of the membrane, a hole, e.g. about 3.5 mm wide, being provided in this sheet to permit application of analyte solution and assay liquids to the membrane. Initially, the membrane is activated by application of a small volume, e.g. about 2 ul, of an aqueous solution containing a known quantity of binding partner for the analyte, followed by drying e.g. by leaving to dry at room temperature. A known volume of the aqueous solution containing the analyte, e.g. about 25 ul, is then applied to the membrane and allowed to pass through into the absorptive pad beneath. An aqueous solution, e.g. 25 ul, containing a known quantity of colloidal gold sol particles labelled with a binding partner for the analyte, which may be the same as or different from that initially applied to the membrane, is then applied and allowed to pass through the membrane.

A small volume of water or buffer may optionally be applied to wash through the gold sol reagent and thus minimise background colour. The quantity of gold sol immobilised on the membrane is then determined by a reflectometer or by the naked eye by comparison with a colour-scale.

In the operation method (6) set out above, the membrane may be sheet material of the desired porosity which may be inert insofar as its only function is to act as a filter. The aggregation of the analyte with the component C may be enhanced by including two or more different binding partners for the analyte to effect a form of cross-linking leading to larger aggregates. Alternatively, the component C may comprise the binding partner for the analyte immobilised on beads, for example monodisperse beads such as Dynospheres (Dyno Particles AS, Oslo, Norway).

The invention also includes kits for carrying out the method of the invention comprising (a) a solid phase onto which a labelled reagent is caused to be immobilised to provide an indication of the presence or quantity of the analyte in the sample and (b) a labelled reagent, characterized in that the labelled reagent comprises a gold sol bound to a substance capable of specifically binding to said analyte or to a specific binding partner therefor, at least 75% by weight of the gold particles of the gold sol having a mean diameter of less than 5 nanometers. A preferred form of kit comprises (a) a solid support for immobilisation of an analyte analogue or a specific binding partner for the analyte or a complex of the analyte with one or more other reagents, (b) said analyte analogue or binding partner and (c) a reagent comprising a gold sol bound to a molecule capable of specifically binding to the analyte or a specific binding partner therefor, at least 75% of the particles of the gold sol having a mean diameter less than 5 nm. Optionally, the solid phase contained in the kit may be a solid support ready for contacting with the analyte by the user, by preliminary coupling of an analyte analogue or a specific binding partner for the analyte to the support. For some assays, such a kit may include a standard amount of the analyte, a standard amount of a specific binding partner therefor and the gold sol reagent. Standard amounts of analyte or specific binding partner or reagent may be in the form of aqueous solutions or, more usually, lyophilised preparations adapted for dissolution at the time of use. In one form of assay, the solid support may be an inert porous membrane which serves to retain a complex of the analyte and a binding partner in aggregated form but permits diffusion of the gold sol reagent, as in method 6 above. In such a system, the size of the analyte complex may be increased by providing said binding partner or analyte analogues attached to relatively large particles e.g. Dynospheres as mentioned above.

The following Examples are given by way of illustration only:

EXAMPLE 1

Colloidal Gold Particles

Particles with a documented mean size less than 5 nm were purchased from Janssen Pharmaceuticals. The average size of the particles was verified to be 4.5 nm with 85% of the particles less than 5 nm, using a sub-micron particle analyser model A4 from Coulter.

The particles were labelled with a mouse monoclonal IgG with specificity for $D_2$, a degradation product of fibrin polymers, using the method described by Slot and Geuze (Eur. J. Cell. Biol. 38: 87–93, 1985). The density of the particle solution was regulated using a buffer; a 1:20 dilution should give an optical density of 2.0 at 580 nm.

Test Device

A 1×1 cm piece of nylon membrane (Hybond N from Amersham with pore size 450 nm) was placed under a strip of white polyvinyl chloride (PVC), 0.28 mm thick and with a 3.5 mm hole centered over the membrane. The membrane was attached to the plastic using double-sided tape. The PVC-strip with the attached membrane was then attached to a 1 mm thick pad of cellulose blotting paper (Schleicher & Schuell) to the tape area not covered by the membrane.

The device was closed underneath by another strip of PVC, 0.40 mm thick, fixed to the pad using double-sided tape. This construction makes it possible for liquid to pass through the hole in the upper PVC-strip, through the membrane and accumulate into the pad.

Activation of Membrane

The membrane was activated by adding 2 ul of a 3.6 mg/ml solution of a second mouse monoclonal IgG, directed against $D_2$. The membrane in the device was allowed to dry at room temperature before use.

Performance of Test 25 ul of plasma possibly containing $D_2$ or plasma enriched with purified $D_2$ was applied on the membrane surface in the test device. After about 1 minute the solution had passed through the membrane and into the pad. 25 ul of the gold solution was then added to the membrane. When this passed through, the presence of $D_2$ in the sample resulted in a reddish colour of gold on the membrane. The intensity of colour was visually related to the concentration of the $D_2$ in the sample, within certain concentration levels. The background colour of controls could be reduced by adding 25 ul of water.

Instrumental Analysis of Test Results

The test results were instrumentally read by employing a reflectometer (Color Eye, Macbeth), attached to an IBM PC and using Macbeth's softwear program. The reflectometer values obtained using this instrument showed, within a certain range, linear correlation between colour intensity and $D_2$-concentration.

EXAMPLE 2

The method of example 1 was repeated using gold colloids with average size of 4.7 nm, 15 nm and 30 nm. All the colloids were purchased from Janssen Pharmaceuticals. The colloids were labelled with antibodies to saturation point (as measured by the procedure of Slot and Geuze).

The colloid suspensions were all diluted to $OD_{525}$=0.1 using 2 mmol/l sodium phosphate buffer (pH 6.4).

The test was performed as in example 1 for each particle size. Positive results gave a colour on the solid membrane which was about the same intensity for the 15 and 30 nm colloids. This intensity was about half the intensity of the 4.7 nm colloid. Measurements by reflectometry, as in example 1, confirmed our visual findings.

EXAMPLE 3

The methods and set up of example 2 were repeated with a mouse monoclonal antibody directed against human C-reactive-protein (CRP). Since CRP is a pentamer, the same antibody was used in the membrane (5 mcl containing 2 mcg of antibody was added) as well as on the gold conjugates. The sample added to the membrane was a human serum containing about 40 mcg CRP/ml diluted 15 times in distilled water. 20 mcl was added to the membrane followed by 20 mcl of the colloidal gold conjugates saturated with antibody and diluted as in example 2. The results were about the same as in example 2 showing that the intensity of the colour formed with 4.7 nm gold was at least 1.5 times the intensity formed with either of 15 nm or 30 nm gold colloid.

EXAMPLE 4

The method and set up of example 2 were repeated using gold colloids with an average size of about 3, 4 and 4.5 nm. The colloids were made according to the method of M ühlpfordt (1982, Experientia 38, pp 1127–28) by increasing the amounts of tannic acid in order to reduce the particle size. The particle sizes were verified by electron microscopy. Since the titration of such small particles with respect to antibody saturation was likely to be difficult, the titration was performed with the 4.5 nm particles and the same amount of antibody was used with 3 and 4 nm. The method was in all other respects the same as that described in example 2. The results showed that the colour produced was slightly more intense with 3 nm than with 4 nm gold colloids which in turn was equal to 4.5 nm.

It should be noted that the handling of 3 nm gold colloid conjugates in washing procedures required the use of an ultracentrifuge in order to sediment the very small particles. In all other ways, the performance of these particles were equal to those of the 4 and 4.5 nm particles.

EXAMPLE 5

15 nm and 30 nm colloidal gold (purchased from Janssen Parmaceuticals, Belgium) and 4.5 nm gold particles made by the method as described in example 4 were used. The colloids were conjugated to mouse monoclonal IgG specific for $D_2$, as described in example 1. The colloidal gold conjugates were finally diluted to $OD_{525}$=0.010 using 2 mmol/l sodium phosphate buffer (pH 6.4).

Membranes of about 0.5×2.0 cm made from Hybond C (Amersham UK) were dotted with 10 mcl of $D_2$ (0.5 mg/ml in 0.15 mol/l NaCl) and dried for about 30 minutes. Free binding sites were then blocked by incubating the membranes with 2 ml of 1% bovine serum albumin in phosphate-buffered saline (pH 7.4) for 30 minutes.

Seven membranes were tested for each size of gold colloid. Each membrane as prepared above was placed in a respective test-tube to which was added 2 ml of one of the diluted colloidal gold conjugates. The membranes were removed from the tubes at appropriate time intervals, rinsed with phosphate-buffered saline and dried. The amount of gold colloid was measured using a reflectometer as in example 1.

The results showed that the development of colour in the test tubes with 4.5 nm gold colloids was more than three times greater than for the 15 nm or the 30 nm gold colloid. The 15 nm and 30 nm gave a very similar set of results to each other.

EXAMPLE 6

Example 5 was repeated using a complete sandwich. The membranes were dotted with a monoclonal mouse IgG specific for $D_2$ (10 mcl containing a total of 5 mcg antibody) and dried.

The membranes were then blocked and incubated with 2 ml of a solution containing 0.1 mg/ml purified $D_2$ in phosphate-buffered saline (pH 7.4) containing 1% bovine serum albumin, for one hour at 37° C. The membranes were then rinsed and incubated with gold colloid conjugates according to the procedure in example 5.

A similar result was obtained showing that the colour development using 4.5 gold colloid conjugate was about twice the intensity obtained with either of the 15 nm or 30 nm colloids.

EXAMPLE 7

Example 6 was repeated replacing two $D_2$-specific antibodies with the same CRP-specific antibody in the membrane as well as on the gold conjugates. The procedure and media were in all other instances identical.

The colour development of 4.5 nm gold colloid conjugates was about three times the intensity obtained with 15 nm gold which in turn was about 1.2 times more intense than 30 nm gold.

EXAMPLE 8

Two mouse monoclonal antibodies specific for $D_2$ as used in the previous examples, were treated as follows:

One of the antibodies was conjugated to gold colloids of 4.5 nm, 15 nm and 30 nm, respectively. The colloids were obtained in the same manner as in example 5. The conjugates were made as in example 5 and diluted to $OD_{525}=$ 0.010 in 50 mmol/l Tris HCl buffer (pH 7.4) containing 0.15 mol/l NaCl, 0.01% Tween 20 and 1% bovine serum albumin.

The second antibody was conjugated to 3 micron particles (Dynospheres CA-031-A, Dyno Particles AS, Norway). The particles were preactivated for protein coupling by the manufacturer. The antibody was dissolved to 170 mcg/ml in 10 mmol/l sodium phosphate buffer (pH 7.5) with 0.15 mol/l NaCl and 30 mg/ml of the particles. To this mixture was added a half volume of 0.05 mol/l of sodium-borate buffer (pH 9.5) and the mixture was end-over-end rotated for 20 hours at 20° C. The particles were thereafter washed, centrifuged, and resuspended in a phosphate buffer (pH 7.5). Any remaining active groups were blocked by incubation with 1 mol/l ethanolamine (pH 9.5) containing 0.1% Tween 20 at 20° C. for another 20 hours. The particles were then washed twice with 50 mmol/l Tris HCl (pH 7.4) containing 0.1 mol/l NaCl, 0.01% bovine serum albumin, and 0.1% Tween 20.

The particles made this way may stay in a homogenous suspension for at least one hour. One mg of particles will bind approximately 5 mcg of antibody.

Aliquots of about 1 mg of particles were centrifuged and resuspended in 0.5 ml of each of the three gold colloid conjugate solutions adjusted to 0.1 mg/ml of purifed $D_2$ and incubated by end-over-end mixing at 20° C. At certain time intervals aliquots of 50 mcl were withdrawn from the mixtures and added to a test device as described in example 1 having a membrane totally blocked with bovine serum albumin.

Using this procedure the gold colloid conjugates will stick to the particles and upon filtration in the device the coloured gold colloids will be arrested in the filter. Unbound colloidal gold conjugates will pass through the filter.

During half an hour of incubation aliquots were withdrawn every fifth minute. The intensity of the colour formed with 15 nm or 30 nm colloids was almost the same at all points, increasing linearly to about 20 minutes. The intensity produced with 4.5 nm colloids was about 2.5 times higher after 5 minutes and this difference in intensity declined after 10 minutes.

It can be seen from the examples given above that gold colloids having a mean diamter of less than 5 nm, allow for quicker reaction kinetics and provide more intense colour development than prior art gold colloid conjugates.

We claim:

1. A method for the qualitative or quantitative determination of an analyte in a test sample wherein a reagent comprising a gold sol bound to a substance capable of specifically binding to said analyte or to a specific binding partner therefor, is caused to be immobilized in bound form on a membrane support to provide an indication of the presence or quantity of the analyte in the sample by detection of the presence of intensity of color of immobilized gold sol, wherein an absorbent pad is located on said membrane support, a liquid impermeable sheet is located on the face of said absorbent pad remote from said membrane support, and a liquid impermeable sheet having one or more holes therein is located on the face of said membrane support remote from said absorbent pad, whereby the test sample and reagent are applied successively to one of said holes and are caused to diffuse transversely through said membrane support by absorption into said absorbent pad, and at least 75% by weight of the gold particles of the gold sol have a mean diameter of less than 5 nanometers and not less than 3 nanometers with the provision that the analyte and the substance capable of specifically binding to the analyte are an antigen/antibody or hapten/antibody pair.

2. A method according to claim 1, wherein at least 80% by weight of the gold particles of the gold sol have a mean diameter of less than 5 nanometers.

3. A method according to claim 1, wherein at least 85% by weight of the gold particles of the gold sol have a mean diameter of less than 5 nanometers.

4. A method according to claim 1, wherein at least 85% by weight of the gold particles of the gold sol have a mean diameter of not less than 3 nanometers.

5. A method according to claim 1, wherein the average gold particle mean diameter is not less than 4 nanometers.

6. A method according to claim 1, wherein the average gold particle mean diameter is not less than 4 nanometers and not greater than 4.5 nanometers.

7. A kit for the qualitative or quantitative determination of an analyte in a liquid test sample comprising (a) a porous membrane support for the passage of said liquid test sample therethrough and onto which a labelled reagent is caused to be immobilized to provide an indication of the presence or quantity of the analyte in the sample, wherein an absorbent pad is located on said membrane support, a liquid impermeable sheet is located on the face of said absorbent pad remote from said membrane support and a liquid impermeable sheet having one or more holes therein is located on the face of said membrane support remote from said absorbent pad, and (b) a labelled reagent comprising a gold sol bound to a substance capable of specifically binding to said analyte or to a specific binding partner therefor, at least 75% by weight of the gold particles of the gold sol having a mean diameter of less than 5 nanometers and not less than 3 nanometers said absorbent pad effective to cause transverse diffusion of said test sample and labelled reagent through said membrane support when applied to one of said holes, with the provision that the analyte and substance capable of specifically binding to the analyte are an antigen/antibody or hapten/antibody pair.

8. A kit according to claim 7 wherein a substance capable of specifically binding to said analyte or a specific binding partner therefor is coupled to the membrane support.

9. A kit according to claim 7 wherein said substance capable of specifically binding to said analyte or a specific binding partner therefor is selected from the group consisting of antibodies and antigens.

10. A kit according to claim 7 wherein said labelled reagent comprises antibodies or antigens.

11. A kit according to claim 7 wherein the membrane support material is selected from nitrocellulose, paper, cellulose acetate, nylon or other polymeric material to which biological substances may bind.

* * * * *